(12) United States Patent
Miyagawa (10) Patent No.: US 8,134,121 B2
(45) Date of Patent: Mar. 13, 2012

(54) CHROMATOGRAPHIC MASS SPECTROMETER

(75) Inventor: Haruhiko Miyagawa, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 412 days.

(21) Appl. No.: 12/444,923

(22) PCT Filed: Oct. 31, 2006

(86) PCT No.: PCT/JP2006/321758
§ 371 (c)(1),
(2), (4) Date: Apr. 9, 2009

(87) PCT Pub. No.: WO2008/053531
PCT Pub. Date: May 8, 2008

(65) Prior Publication Data
US 2010/0102216 A1    Apr. 29, 2010

(51) Int. Cl.
*B01D 53/02* (2006.01)
*B01D 59/44* (2006.01)
(52) U.S. Cl. ............................ 250/282; 73/23.37; 95/82
(58) Field of Classification Search ................ 73/23.37; 95/82; 96/101, 106; 250/281, 282
See application file for complete search history.

(56) References Cited

U.S. PATENT DOCUMENTS

| | | | |
|---|---|---|---|
| 4,507,555 A * | 3/1985 | Chang | 250/281 |
| 5,958,246 A * | 9/1999 | Tipler et al. | 210/656 |
| 6,329,652 B1 * | 12/2001 | Windig et al. | 250/282 |
| 6,717,130 B2 * | 4/2004 | Bateman et al. | 250/282 |
| 7,230,233 B2 * | 6/2007 | Whitney et al. | 250/282 |
| 7,279,679 B2 * | 10/2007 | Old et al. | 250/282 |
| 7,800,055 B2 * | 9/2010 | Geromanos et al. | 250/288 |
| 2006/0125826 A1 * | 6/2006 | Lubkowitz et al. | 345/440 |
| 2008/0234948 A1 * | 9/2008 | Walk et al. | 702/23 |

FOREIGN PATENT DOCUMENTS

| | | |
|---|---|---|
| EP | 1 203 953 A2 | 5/2002 |
| JP | 60-004852 A | 1/1985 |
| JP | 04-144051 A | 5/1992 |
| JP | 2002-139484 A | 5/2002 |
| JP | 2006-292446 A | 10/2006 |

\* cited by examiner

*Primary Examiner* — Robert Clemente
(74) *Attorney, Agent, or Firm* — Sughrue Mion, PLLC

(57) ABSTRACT

A chromatographic mass spectrometer 100, 150 is provided with a measuring portion 21 for measuring n-alkane of a number of different carbon numbers, and characterized by further having: a mass number storing portion 31 for storing the mass number for each n-alkane; and a mass chromatogram preparing portion 22 for preparing a mass chromatogram for each mass number by focusing on the mass number on the basis of the mass spectrum.

2 Claims, 8 Drawing Sheets

CHROMATOGRAPHIC MASS SPECTROMETER

TECHNICAL FIELD

The present invention relates to a chromatographic mass spectrometer, and in particular, to a chromatographic mass spectrometer for measuring the retention time for n-alkane.

BACKGROUND TECHNOLOGY

Gas chromatographic mass spectrometers (GC/MS) are made up of a gas chromatographic apparatus (GC) and a mass spectrometer (MS). Thus, first respective substances to be measured included in the substance (sample), which is the object of analysis, are separated along the time axis using a gas chromatographic apparatus. Next, the respective substances to be measured separated along the time axis are measured using a mass spectrometer (MS), so that the substances to be measured are separated based on the mass number, and thus detected. Measurement is repeated at short time intervals, so that a number of mass spectra having a mass number along the lateral axis and an ion intensity along the longitudinal axis are prepared. In addition, the peaks of a certain mass number in the number of mass spectra are focused, and the focused peaks are aligned along the time axis, so that a mass chromatogram is prepared. Furthermore, all of the peaks in one mass spectrum are integrated and aligned along the time axis, and thus a total ion chromatogram is prepared.

In addition, the retention time for the substance to be measured is determined on the basis of the peak in the total ion chromatogram. Furthermore, in order to calculate the retention index of the substance to be measured, n-alkane of different carbon numbers and the substance to be measured are introduced in the GC/MS, and as a result of measurement, the relationship between the peaks of the n-alkane of different carbon numbers and the peak of the substance to be measured in the total ion chromatogram is found, and thus, the retention index of the substance to be measured is calculated.

Here, unlike the wavelength in spectrometry and the mass number in mass spectrometry, the "retention time" in gas chromatographic apparatuses is not a value that is uniquely determined on the basis of the properties of the substance to be measured, but affected by a number of factors, such as the type, dimensions and temperature of the column, the type, pressure and flow amount of the carrier gas, and the type of apparatus. Meanwhile, the "retention index" is an index depending on the retention time for a predetermined standard substance (generally n-alkane), and has a numeric value which is not affected by the difference in the GC conditions, the column maker, the length, the inner diameter and the film thickness. That is to say, one numeric value is given to each standard substance, and the carbon number×100 is given to n-alkane, so that 1000 is given to n-$C_{10}$ alkane and 1100 is given to n-$C_{11}$ alkane, for example.

Figure 8:
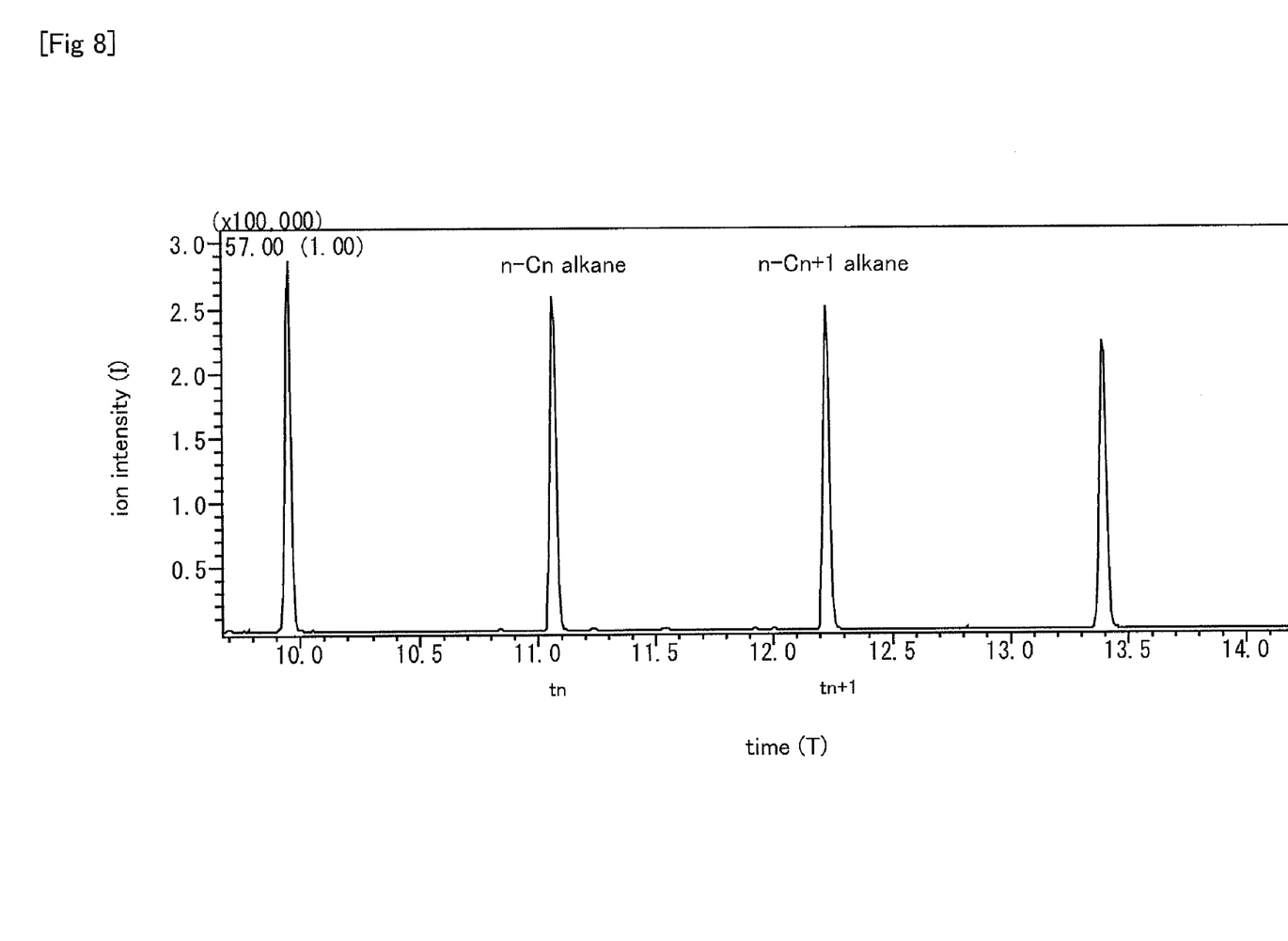
FIG. 8 is a diagram illustrating a method for determining the retention index of the substance to be measured.

Thus, in the case where the peak of the substance to be measured in the total ion chromatogram is between the peak of the n-$C_n$ alkane and the peak of the n-$C_{n+1}$ alkane, for example, the peak of the n-$C_n$ alkane, the peak of the n-$C_{n+1}$ alkane and the peak of the substance to be measured are used to calculate the retention index (ix) of the substance to be measured using the following formula (1) or (2) (see FIG. 8).

(i) At time of analysis at constant temperature $$ix = 100 \cdot (tx - t_n)/(t_{n+1} - t_n) + n \quad (1)$$

(ii) At time of analysis while temperature rising $$ix = 100 \cdot (\log tx' - \log t_n')/(\log t_{n+1}' - \log t_n') + n \quad (2)$$

Here, $i_{n+1}$ is the retention index of the n-$C_{n+1}$ alkane, $i_n$ is the retention index of the n-$C_n$ alkane, $t_{n+1}$ is the retention time for the n-$C_{n+1}$ alkane, $t_n$ is the retention time for the n-$C_n$ alkane, tx is the retention time for the substance to be measured, $t_{n+1}'$ is the corrected retention time for the n-$C_{n+1}$ alkane, $t_n'$ is the corrected retention time for the n-$C_n$ alkane, and tx' is the corrected retention time for the substance to be measured.

When the retention index (ix) of the substance to be measured is gained in this manner, whether or not the mass spectra of the substances registered in a database having holding indices in a certain range including the retention index (ix) of the substance to be measured include mass spectra which are the same or similar to the mass spectrum of the substance to be measured can be determined. Here, reverse searching methods, for example, can be cited as methods for determination. Reverse searching methods are searching methods for calculating the probability of the substance to be measured being a registered substance by calculating to what extent the relative intensity of the peak of the main fragment ions in the mass spectra of the registered substances is similar to the mass spectrum of the substance to be measured.

Conversely, in the case where the retention index (ix) of the substance to be measured is gained in advance, the peak of the n-$C_n$ alkane and the peak of the n-$C_{n+1}$ alkane in the total ion chromatogram can be used to calculate the retention time (ix) for the substance to be measured using the formula (1') or (2'). Thus, the retention time (ix) of the substance to be measured is gained, and the substance to be measured is easy to adopt.

(i) At time of analysis at constant temperature $$tx = \{(ix/100) - n\} \cdot (t_{n+1} - t_n) + t_n \quad (1')$$

(ii) At time of analysis when temperature rising $$\log tx' = \{(ix/100) - n\} \cdot (\log t_{n+1}' - \log t_n') + \log t_n' \quad (2')$$

Patent Document 1: Japanese Unexamined Patent Publication 2003-139755

DISCLOSURE OF THE INVENTION

Problem to be Solved by the Invention

Figure 9:
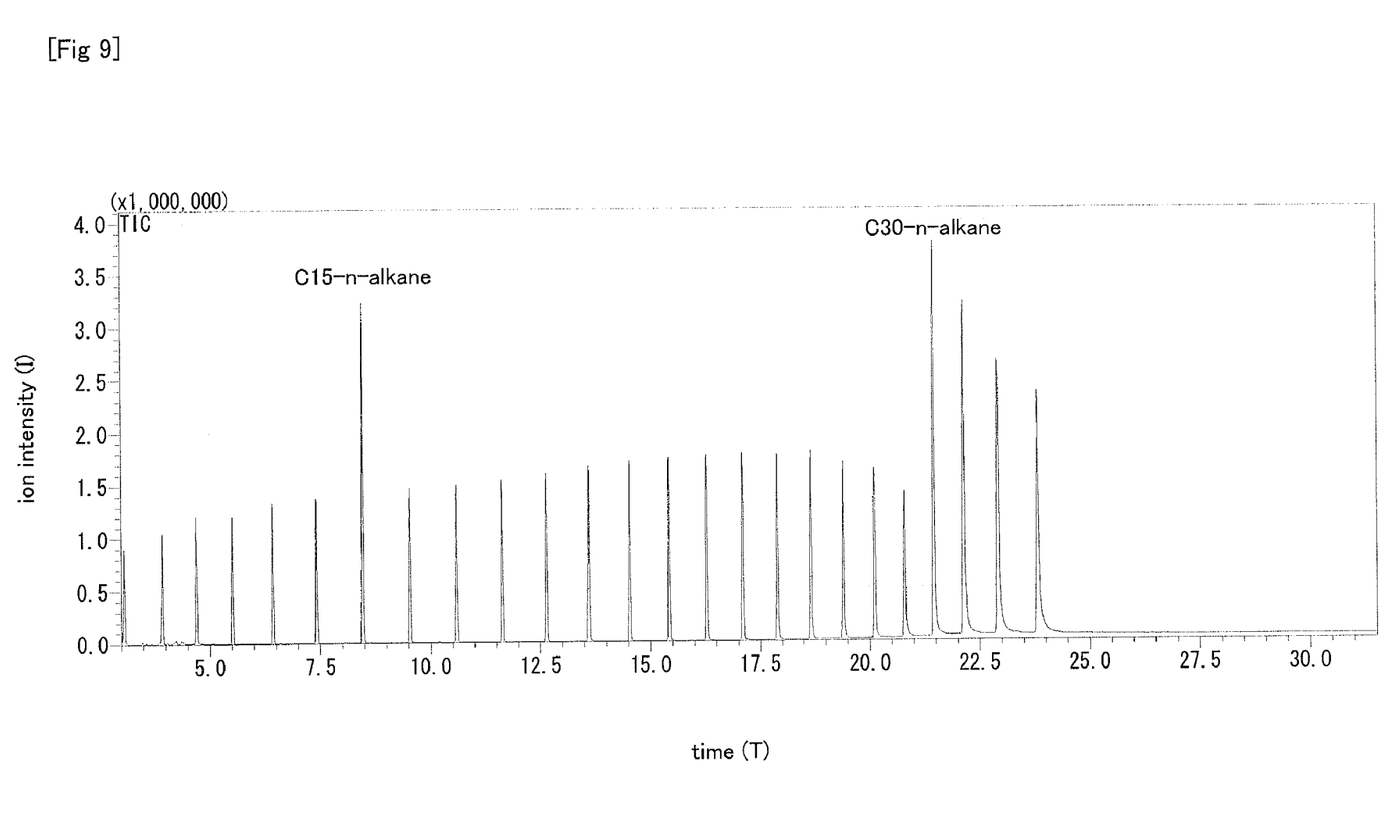
FIG. 9 is a conventional total ion chromatogram used to measure the retention time for n-alkane.

When n-alkane of $C_{10}$ to $C_{33}$ is measured, for example, and a total ion chromatogram is prepared, it is difficult to identify which peak corresponds to the peak of the n-alkane of which carbon number. At this time, the concentration of the n-alkane doubles when the carbon number increases by a certain number, for example the concentration of the n-alkane of $C_{15}$ and $C_{30}$ is two times higher than the concentration of the n-alkane of carbon numbers other than $C_{15}$ and $C_{30}$, so that identification becomes easier. In this case, however, peaks of adjacent n-alkanes cannot be identified with precision, as shown in FIG. 9.

Therefore, an object of the present invention is to provide a chromatographic mass spectrometer with which the retention time for n-alkane of all carbon numbers can be easily determined when the n-alkane of a number of different carbon numbers is measured.

Means for Solving Problem

In the case where n-alkane of a number of different carbon numbers is measured, it is difficult to identify which peak corresponds to the peak of the n-alkane of which carbon number in total ion chromatograms. However, there is one peak where the ion intensity is extremely high for each carbon number in mass chromatograms, and therefore, it can be found that the peak where the ion intensity is the maximum in the mass chromatogram prepared focusing on the mass number 170, for example, is determined to be the peak of the n-alkane of $C_{12}$ having this mass number (molecular weight) 170, while the peak where the ion intensity is the maximum in the mass chromatogram prepared focusing on the mass number 254, for example, is determined to be the peak of the n-alkane of $C_{18}$ having this mass number (molecular weight) 254, and thus, the peak where the ion intensity is the maximum in mass chromatogram prepared focusing on a predetermined mass number can be determined to be the peak of the n-alkane having this predetermined mass number (molecular weight) (see FIGS. 2 and 3).

That is to say, the chromatographic mass spectrometer according to the present invention is a chromatographic mass spectrometer provided with a measuring portion for measuring n-alkane of a number of different carbon numbers, and further has: a mass number storing portion for storing the mass number for each n-alkane; and a mass chromatogram preparing portion for preparing a mass chromatogram for each mass number by focusing on the mass number on the basis of the mass spectrum.

In accordance with the chromatographic mass spectrometer according to the present invention, a mass chromatogram is prepared for each mass number by focusing on the mass number. At this time, one peak can be easily identified where the ion intensity becomes the maximum in each mass chromatogram. Thus, the peak where the ion intensity becomes the maximum in the mass chromatogram prepared focusing on a predetermined mass number can be determined to be the peak of the n-alkane having the predetermined mass number. As a result, the retention time for each n-alkane can be determined, and thus, the retention index for the substance to be measured can be calculated using the formula (1) or (2), by measuring the retention time of the substance to be measured, for example. Alternatively, the retention time for the substance to be measured may be calculated using the formula (1') or (2'), in the case where the retention index for the substance to be measured is known.

Other Means for Solving Problem and Working Effects

In addition, the chromatographic mass spectrometer according to the present invention is a chromatographic mass spectrometer further having; a display; and a mass chromatogram displaying portion for displaying an image on the above described display for each mass chromatogram with the lateral axis indicating a common time for each mass chromatogram and the longitudinal axis indicating the ion intensity shifting with constant intervals for each mass chromatogram.

In accordance with the chromatographic mass spectrometer according to the present invention, an image can be displayed on the display for each mass chromatogram with the coordinates translated. At this time, the operator can easily identify one peak where the ion intensity is the maximum in each mass chromatogram. Therefore, the operator can determine that the peak where the ion intensity becomes the maximum in the mass chromatogram prepared focusing on a predetermined mass number is the peak of the n-alkane having the predetermined mass number. As a result, the operator can determine the retention time for each n-alkane, and therefore, the retention index of the substance to be measured can be calculated using the formula (1) or (2), by measuring the retention time for the substance to be measured. Alternatively, the retention time of the substance to be measured may be calculated using the formula (1') or (2') in the case where the retention index of the substance to be measured is known.

In addition, in the chromatographic mass spectrometer according to the present invention, the mass chromatogram displaying portion may display images on said display for all of the mass chromatograms.

In addition, the chromatographic mass spectrometer according to the present invention may further have a determining portion for determining that the peak where the ion intensity becomes the maximum in the mass chromatogram prepared focusing on a predetermined mass number is the peak for n-alkane having a predetermined mass number.

In accordance with the chromatograph mass spectrometer according to the present invention, one peak where the ion intensity becomes the maximum can be identified in each mass chromatogram. Therefore, the chromatographic mass spectrometer can determine that the peak where the ion intensity becomes the maximum in the mass chromatogram prepared focusing on a predetermined mass number is the peak of the n-alkane having the predetermined mass number. As a result, the chromatographic mass spectrometer can determine the retention time for each n-alkane, and thus, the retention index of the substance to be measured can be calculated using the formula (1) or (2) when the retention time for the substance to be measured is measured, for example. Alternatively, the retention time of the substance to be measured may be calculated using the formula (1') or (2') in the case where the retention index of the substance to be measured is known.

In addition, the chromatographic mass spectrometer according to the present invention may further have: a display; and an information displaying portion for displaying the retention time and the retention index of each n-alkane on the above described display.

EXPLANATION OF SYMBOLS 1 chromatographic apparatus (GC)
5 mass spectrometer (MS)
11 CPU (data processing unit)
12 memory (external storing unit)
20, 70 computer
21 measuring portion
100, 150 chromatographic mass spectrometer

BEST MODE FOR CARRYING OUT THE INVENTION

In the following, the embodiments of the present invention are described in reference to the drawings. Here, the present invention is not limited to the following embodiments, and needless to say, various modifications may be included in the scope, providing that they do not deviate from the gist of the present invention.

First Embodiment

Figure 1:
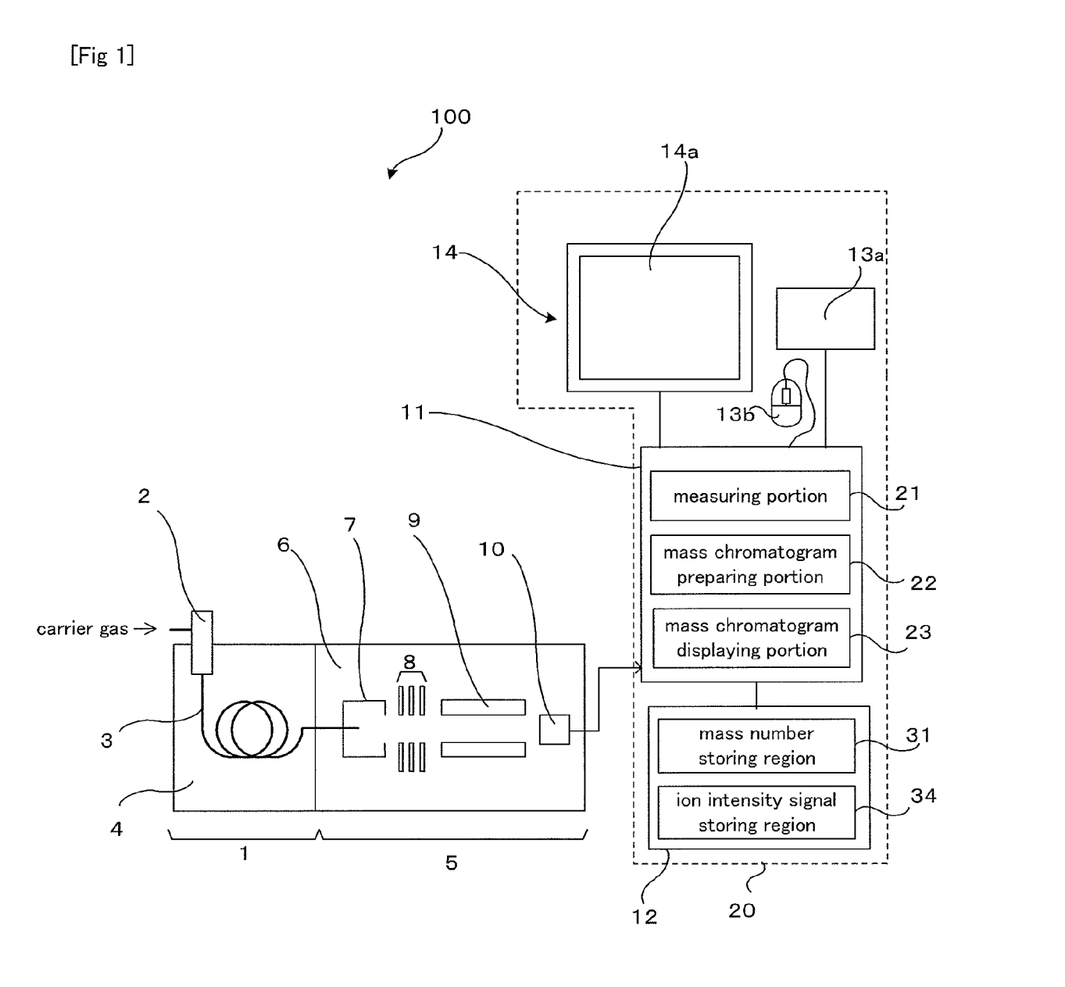
FIG. 1 is a diagram showing the configuration of a GC/MS apparatus according to the present invention.

FIG. 1 is a diagram showing the configuration of a GC/MS apparatus according to the present invention. The GC/MS apparatus 100 is made up of a GC 1, an MS 5 and a computer 20.

The GC 1 is made up of a column oven 4, a column 3 contained within the column oven 4 and a sample injecting portion 2 connected to an entrance end of the column 3. A sample gas (sample) which is the object of analysis is introduced into the column 3 from the sample injecting portion 2 when pushed by a carrier gas. As a result, the respective substances to be measured included in the sample gas are separated along the time axis while passing through the column 3, and reach the exit end of the column 3. Here, the exit end of the column 3 is connected to the MS 5.

The MS 5 is provided with an ion source 7 which is connected to the exit end of the column 3, an ion lens 8, a quadrupole filter 9 to which a voltage is applied, and a detector 10, within an analysis chamber 6 from which air is discharged so that the inside becomes a vacuum. The respective substances to be measured which flow out from the column 3 in sequence are ionized in the ion source 7 as a result of collision with electrons or chemical reaction. Consequently, the generated ions fly out from the ion source 7 so as to be condensed by the ion lens 8 and accelerate appropriately, and after that introduced into the space of the quadrupole filter 9 in the longitudinal direction.

Only ions having a mass number (mass m/charge z) in accordance with the applied voltage pass through the quadrupole filter 9 to which a voltage gained when a direct current voltage and a high frequency voltage overlap is applied, and thus, selected ions reach the detector 10. At this time, the mass number of ions that pass through the quadrupole filter 9 depends on the applied voltage, and therefore, an ion intensity signal for ions having a predetermined mass number can be gained in the detector 10 by scanning the applied voltage. Here, the output of the detector 10 is inputted into the computer 20.

The computer 20 is provided with a CPU (data processing unit) 11, and in addition, a memory (external storing unit) 12, a keyboard 13a and a mouse 13b, which are input units, and a display 14 having a monitor screen 14a are connected to the computer.

The function in terms of the processing of the CPU 11 is illustrated as blocks when a measuring portion 21, a mass chromatogram preparing portion 22 and a mass chromatogram displaying portion 23 are provided. The measuring portion 21 stores the ion intensity signal acquired by the detector 10 in an ion intensity signal storing region 34 in the memory 12.

In addition, the memory 12 has a mass number storing region 31 which stores the name of respective n-alkanes and their mass numbers (molecular weight), and an ion intensity signal storing region 34.

The measuring portion 21 controls the preparation of a mass spectrum by taking the ion intensity when mass scanning is carried out for a certain retention time along the longitudinal axis and the mass number along the lateral axis, for example. At this time, mass scanning can be intermittently repeated in sequence at constant intervals, so that a great number of mass spectra can be acquired in correspondence to the respective substances to be measured, which flow out in sequence from the column 3.

The mass chromatogram preparing portion 22 spreads the ion intensity along the time axis focusing on a certain mass number, so that it can be sampled on the basis of the mass spectra stored in the ion intensity signal storing region 34, and thus, controls the preparation of a mass chromatogram. At this time, each mass chromatogram is prepared focusing on the mass number of the n-alkane stored in the mass number storing region 31. The same number of mass chromatograms as the number of types of n-alkane measured are prepared, so that a mass chromatogram is prepared focusing on the mass number 170 of the n-alkane of $C_{12}$ (see FIG. 2) and a mass chromatogram is prepared focusing on the mass number 254 of the n-alkane of $C_{18}$ (see FIG. 3), for example.

Figure 4:
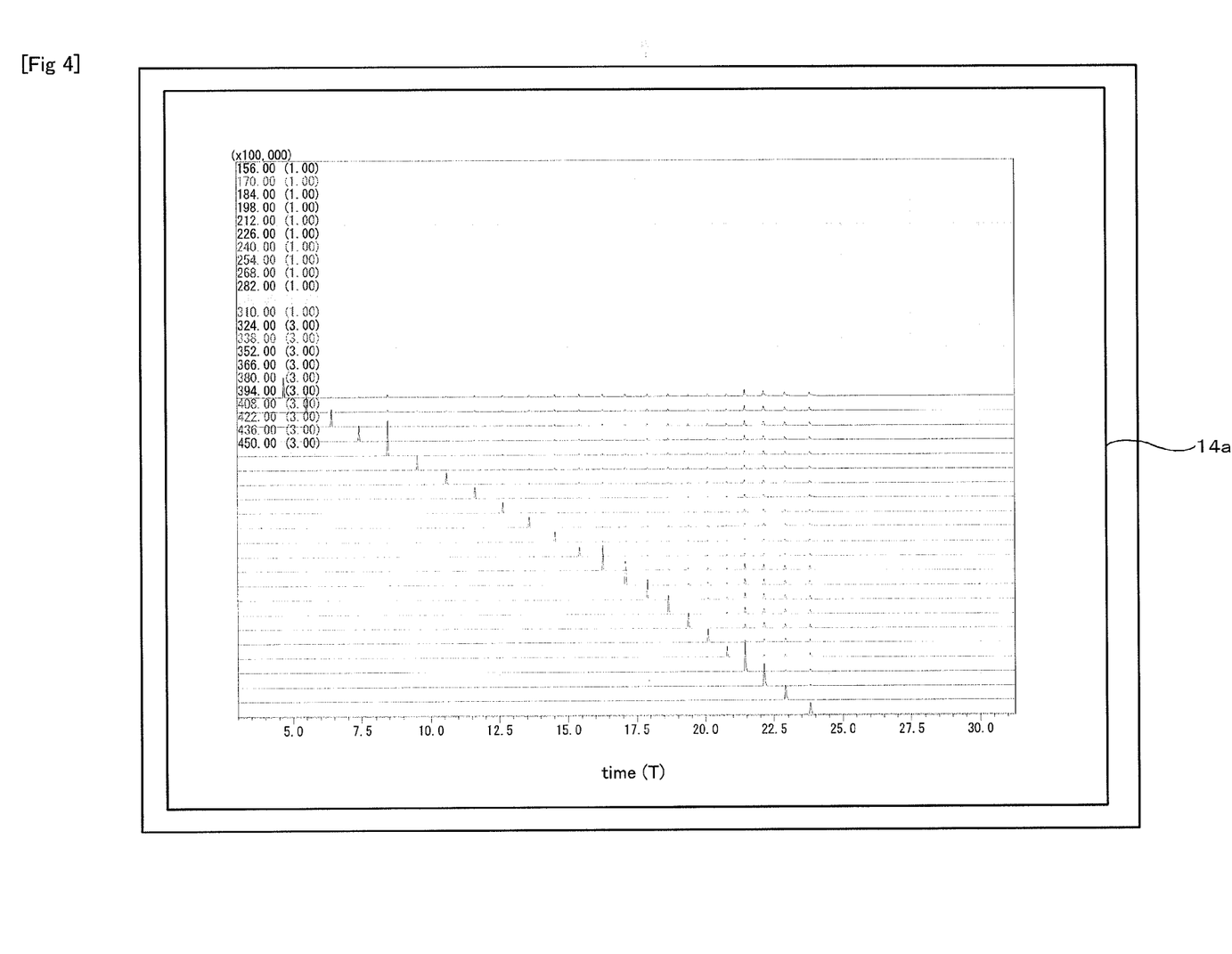
FIG. 4 is a diagram showing an example of the screen on the monitor displaying an image.

The mass chromatogram displaying portion 23 carries out an arithmetic operation on the basis of each mass chromatogram and outputs the results on the monitor screen 14a under control. At this time, an image is displayed on the monitor screen 14a, for example, for all of the mass chromatograms, where the lateral axis indicates a common time for all of the mass chromatograms and the longitudinal axis indicates the ion intensity that shifts with constant intervals for the respective mass chromatograms. In addition, an image is also displayed for the mass number that is focused at the time of preparation for each mass chromatogram (see FIG. 4). Here, as shown in FIG. 4, the ion intensity at the peak of time 5.4 min becomes the maximum in the mass chromatogram prepared focusing on the mass number 170 of the n-alkane of $C_{12}$, and the ion intensity at the peak of time 11.6 min becomes the maximum in the mass chromatogram prepared focusing on the mass number 254 of the n-alkane of $C_{18}$.

Figure 5:
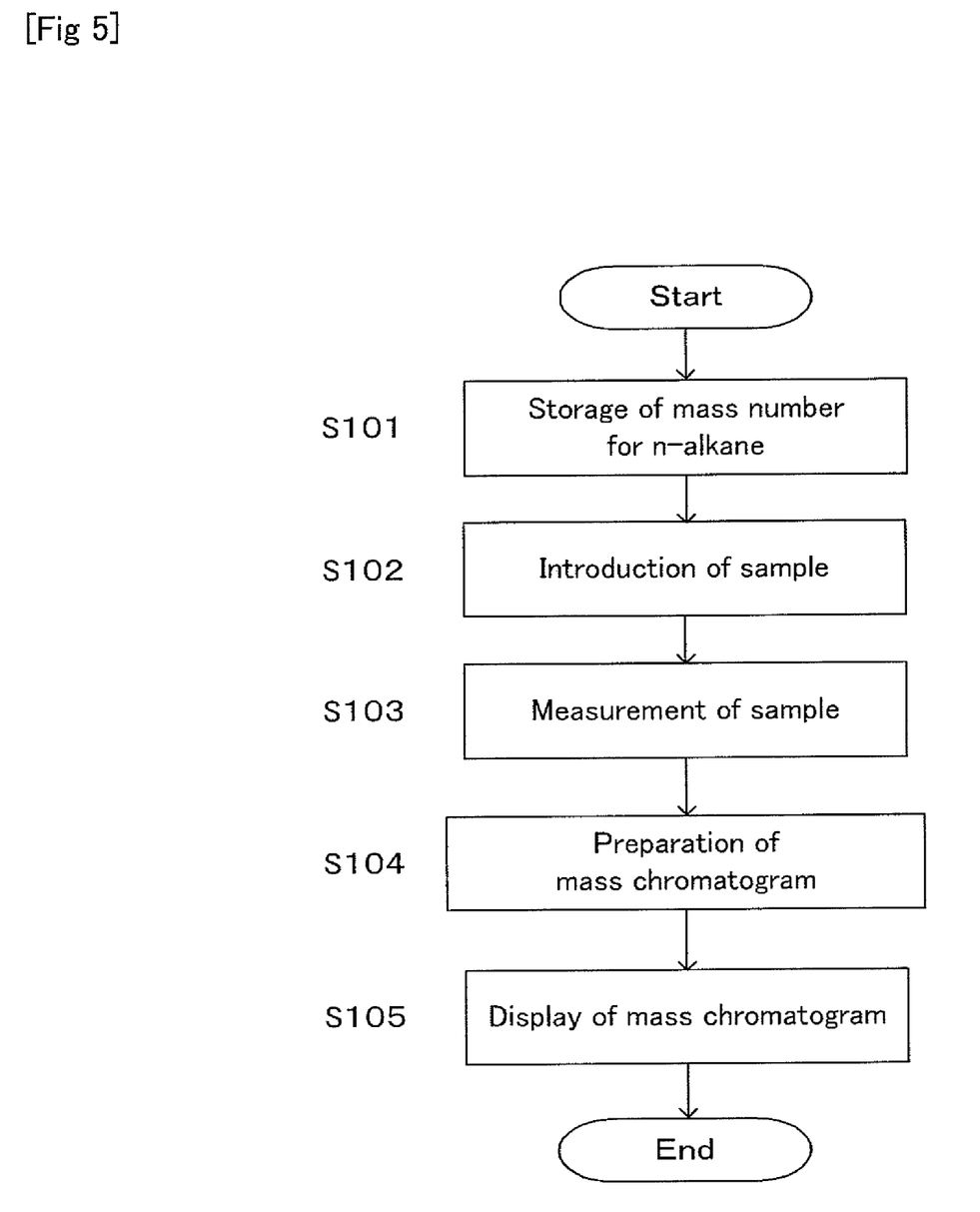
FIG. 5 is a flow chart showing the procedure for the measuring method.

Next, a measuring method for measuring the retention time for n-alkane is described. FIG. 5 is a flow chart showing the procedure for the measuring method.

First, in the process in the step S101, the measuring portion 21 uses an input apparatus to store the names of the n-alkane of $C_{10}$ to $C_{33}$ and the mass numbers (molecular weight) in the mass number storing region 31 in such a manner as they correspond to each other. Each n-alkane is stored with its mass number, so that the n-alkane of $C_{12}$ has a mass number 170 and the n-alkane of $C_{18}$ has a mass number 254, for example.

Next, in the process in the step S102, a constant amount of a sample gas (sample) containing n-alkane of $C_{10}$ to $C_{33}$ is introduced into the column 3 from the sample injecting portion 2.

Next, in the process in the step S103, the mass scanning is intermittently repeated in sequence with constant intervals, so that a mass spectrum can be gained and stored in the ion intensity signal storing region 34.

Figure 2:
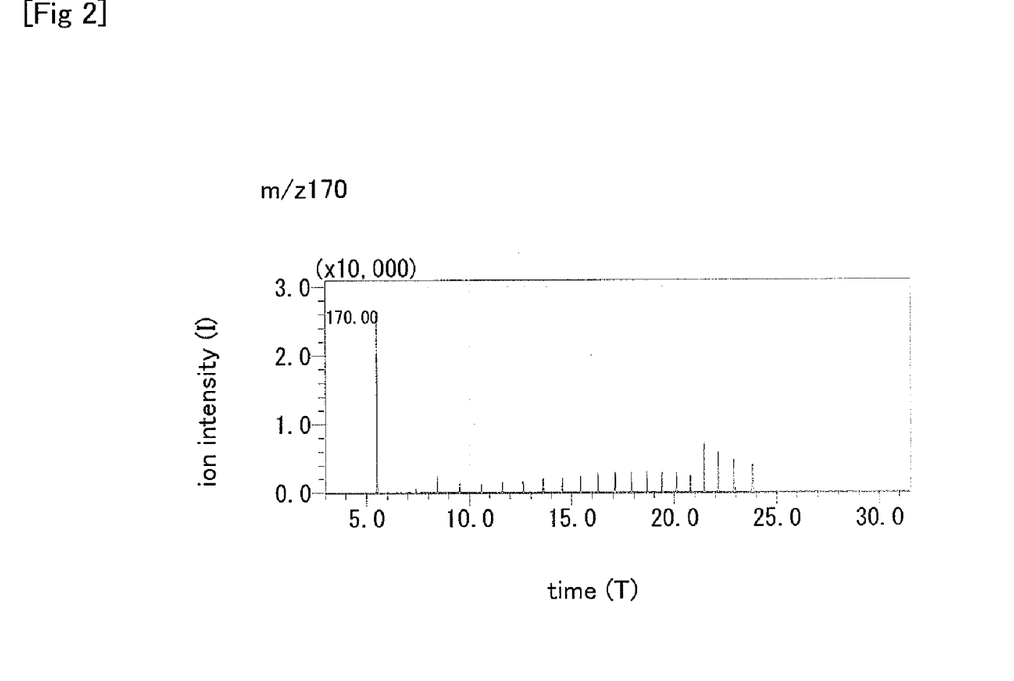
FIG. 2 is a mass chromatogram prepared focusing on the mass number 170 of the n-alkane of $C_{12}$.
Figure 3:
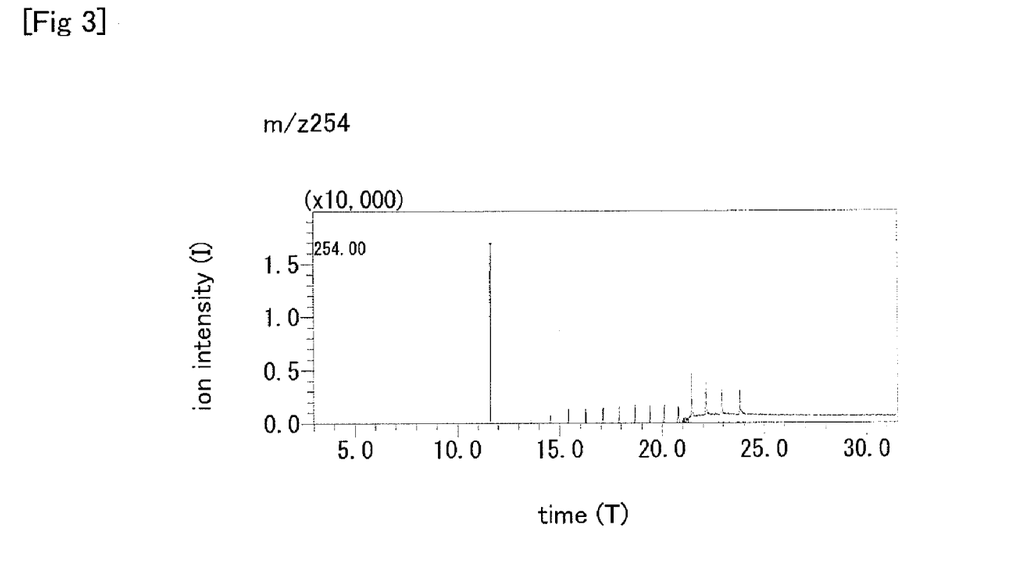
FIG. 3 is a mass chromatogram prepared focusing on the mass number 254 of the n-alkane of $C_{18}$.

Next, in the process in the step S104, the mass chromatogram preparing portion 22 prepares respective mass chromatograms focusing on the mass number of each n-alkane, which is stored in the mass number storing region 31, on the basis of the mass spectrum (see FIGS. 2 and 3).

Next, in the process in the step S105, the mass chromatogram displaying portion 23 carries out an arithmetic operation on the basis of each mass chromatogram and outputs the results on the monitor screen 14a. At this time, the monitor screen 14a displays an image for all of the mass chromatograms with the lateral axis indicating a common time for all of the mass chromatograms and the longitudinal axis indicating the ion intensity which shifts with constant intervals for each mass chromatogram, for example. In addition, an image is also displayed for the mass number focused at the time of preparation for each mass chromatogram (see FIG. 4).

After that, the process in the step S105 is completed, and thus, the present flow chart is completed.

As described above, the GC/MS apparatus 100 according to the present invention can display an image for all of the mass chromatograms on the monitor screen 14a. At this time, the operator can easily identify one peak where the ion intensity becomes the maximum in each mass chromatogram. Accordingly, the operator can determine that the peak where the ion intensity becomes the maximum in the mass chromatogram prepared focusing on a certain mass number is the peak of the n-alkane having the predetermined mass number. As a result, the operator can determine the retention time for each n-alkane, and therefore, the retention index of the substance to be measured can be calculated using the formula (1) or (2) when the retention time for the substance to be measured is measured. Alternatively, the retention time for the substance to be measured may be calculated in the GC/MS apparatus 100 using the formula (1') or (2'), in the case where the retention index for the substance to be measured is known.

Second Embodiment

Figure 6:
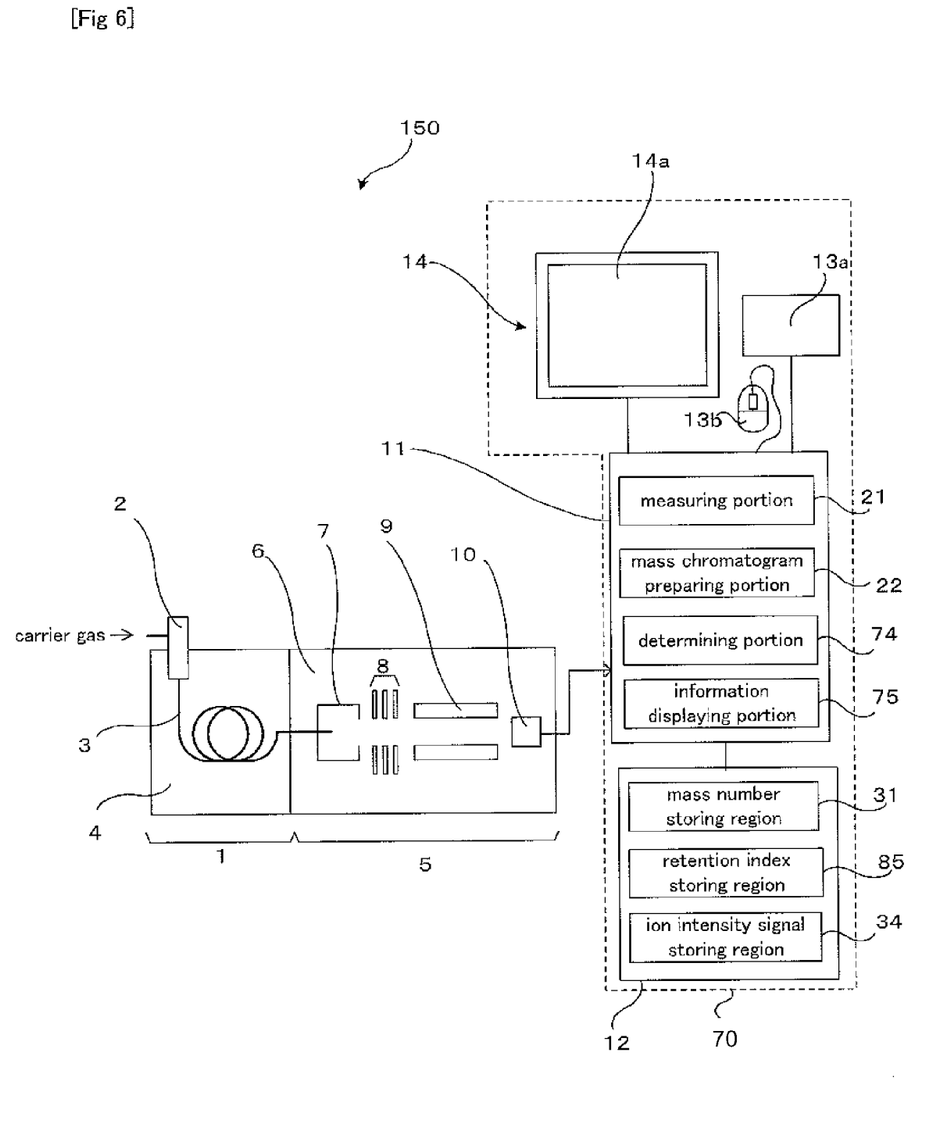
FIG. 6 is a diagram showing the configuration of another GC/MS apparatus according to the present invention.

FIG. 6 is a diagram showing the configuration of a GC/MS apparatus according to the present invention. Here, the same symbols are used for components which are the same as in the first embodiment, and the descriptions thereof are omitted. The GC/MS apparatus 150 is made up of a GC 1, an MS 5 and a computer 70.

The computer 70 is provided with a CPU (data processing unit) 11, and in addition, a memory (external storing unit) 12, a keyboard 13a and a mouse 13b, which are input units, and a display 14 having a monitor screen 14a are connected to the computer.

The function in terms of the processing of the CPU 11 is illustrated as blocks when a measuring portion 21, a mass chromatogram preparing portion 22, a determining portion 74 and an information displaying portion 75 are provided.

In addition, the memory 12 has a mass number storing region 31 which stores the name of respective n-alkanes and their mass numbers (molecular weight), an ion intensity signal storing region 34, and a retention index storing region 85 for storing the name of respective n-alkane, as well as their holding indices.

The determining portion 74 determines under control that the peak where the ion intensity becomes the maximum in the mass chromatogram prepared focusing on a predetermined mass number is the peak of the n-alkane having the predetermined mass number. In the mass chromatograph prepared focusing on the mass number (molecular weight) 170 of the n-alkane of $C_{12}$ shown in FIG. 2, for example, the peak at time 5.4 min, where the ion intensity becomes the maximum, is regarded as the peak of the n-alkane of $C_{12}$, while in the mass chromatograph prepared focusing on the mass number (molecular weight) 254 of the n-alkane of $C_{18}$ shown in FIG. 3, the peak at time 11.6 min, where the ion intensity becomes the maximum, is regarded as the peak of the n-alkane of $C_{18}$. Thus, the retention time for the n-alkane of $C_{12}$ can be regarded as being 5.4 min and the retention time for the n-alkane of $C_{18}$ can be regarded as being 11.6 min.

The information displaying portion 75 displays the retention time and the retention index of each n-alkane on the monitor screen 14a on the basis of the retention index stored in the retention index storing region 85 under control. The retention time and the retention index is displayed for each n-alkane, so that n-alkane of $C_{12}$ has a retention time of 5.4 min, and thus, the retention index is shown as 1200, while the n-alkane of $C_{18}$ has a retention time of 11.6 min, and thus, the retention index is shown as 1800, for example.

Figure 7:
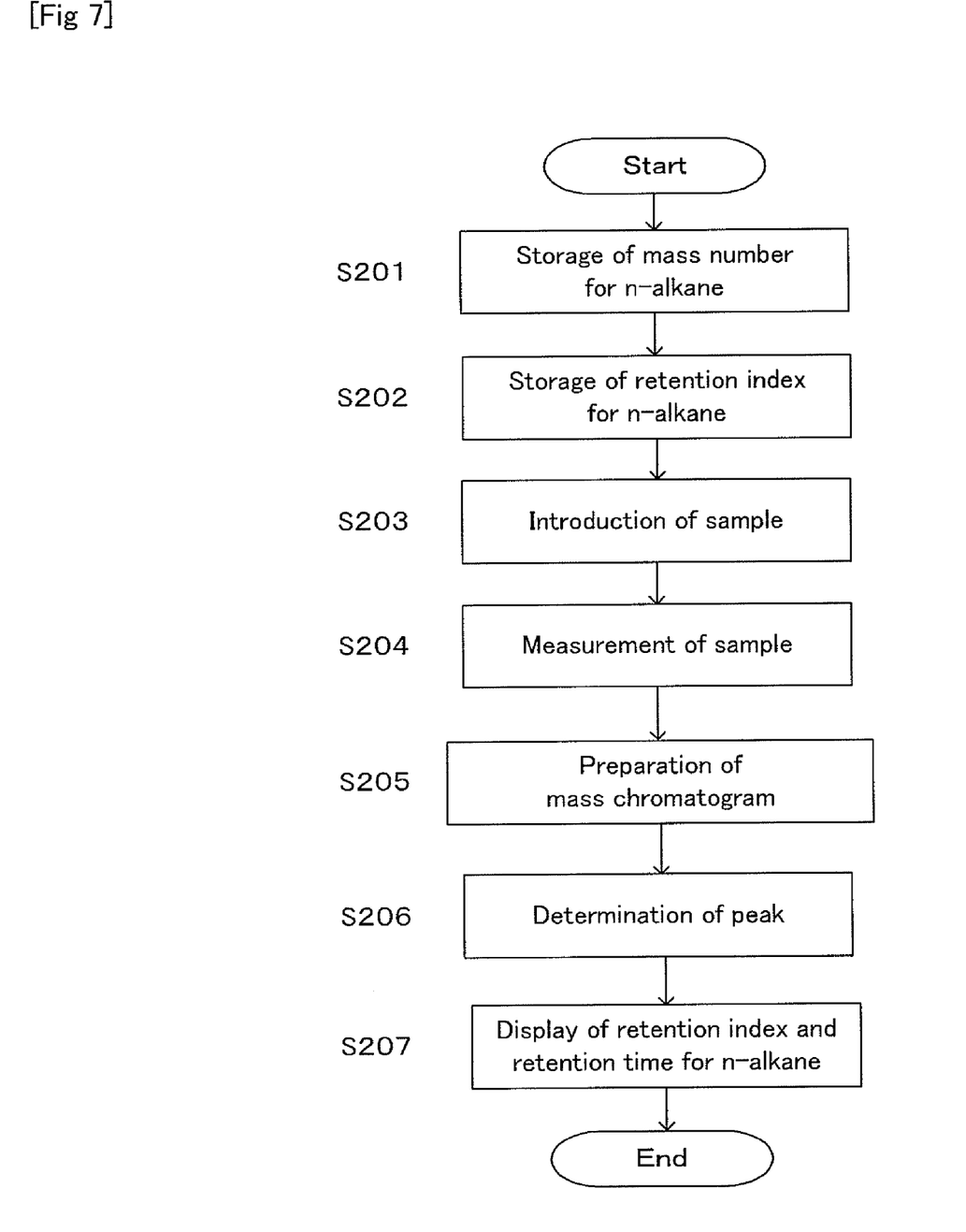
FIG. 7 is a flow chart showing the procedure for the measuring method.

Next, a measuring method for the retention time for n-alkane is described. FIG. 7 is a flow chart showing the procedure of the measuring method.

First, in the process in the step S201, an input apparatus is used so that the name of n-alkanes of $C_{10}$ to $C_{33}$ and the mass number (molecular weight) are stored in the mass number storing region 31 in such a manner that they correspond to each other. Each n-alkane is stored with its mass number, so that the n-alkane of $C_{12}$ has a mass number of 170 and the n-alkane of $C_{18}$ has a mass number of 254, for example.

Next, in the process in the step S202, an input apparatus is used so that the name of n-alkanes of $C_{10}$ to $C_{33}$ and the retention index are stored in the retention index storing region 85 in such a manner that they correspond to each other. Each n-alkane is stored with its retention index, so that the n-alkane of $C_{12}$ has a retention index of 1200 and the n-alkane of $C_{18}$ has a retention index of 1800, for example.

Next, in the process in the step S203, a constant amount of a sample gas (sample) containing n-alkanes of $C_{10}$ to $C_{33}$ is introduced into the column 3 from the sample injecting portion 2.

Next, in the process in the step S204, the measuring portion 21 carries out intermittent mass scanning repeatedly in sequence with constant intervals, and thus acquires a mass spectrum which is then stored in the ion intensity storing region 34.

Next, in the process in the step S205, the mass chromatogram preparing portion 22 prepares each mass chromatogram focusing on the mass number of the n-alkane stored in the mass number storing region 31 on the basis of the mass spectrum (see FIGS. 2 and 3).

Next, in the process in the Step S206, the determining portion 74 determines that the peak where the ion intensity becomes the maximum in the mass chromatogram prepared focusing on the mass number stored in the mass number storing region 31 is the peak of the n-alkane having the same number.

Next, in the process in the step S207, the information displaying portion 75 displays the retention time and the retention index of each n-alkane on the monitor screen 14a on the basis of the retention index stored in the retention index storing region 85. The retention time and the retention index for each n-alkane are displayed so that the n-alkane of $C_{12}$ is shown so as to have a retention time of 5.4 min and a retention index of 1200 and the n-alkane of $C_{18}$ is shown so as to have a retention time of 11.6 min and a retention index of 1800, for example.

After that, the process in the step S207 is completed, and thus, the present flow chart is completed.

As described above, in accordance with the GC/MS apparatus 150 according to the present invention, the determining portion 74 can identify one peak where the ion intensity becomes the maximum in each mass chromatogram. Therefore, the GC/MS apparatus 150 can determine that the peak where the ion intensity is the maximum in the mass chromatogram prepared focusing on a predetermined mass number is the peak of the n-alkane having the predetermined mass number. As a result, the GC/MS apparatus 150 can determine the retention time for each n-alkane, and therefore, the retention time for the substance to be measured can be measured, and thus, the retention index of the substance to be measured can be calculated using the formula (1) or (2), for example. Alternatively, the retention time for the substance to be measured in the GC/MS apparatus 150 may be calculated using the formula (1') or (2'), in the case where the retention index for the substance to be measured is known.

Though the procedure is described using data for n-alkane in the embodiments, the same results can be expected when a different sequence of homologues which can be used for determining the holding indices is used. As examples, n-alkylbis(trifluoromethyl)phosphine sulfides and 1-(N,N-diisopropylamino)-alkanes can be cited.

INDUSTRIAL APPLICABILITY

The present invention can be used in gas chromatographic mass spectrometers for measuring the retention time of n-alkane.

The invention claimed is:

1. A method of chromatographic mass spectrometry, comprising:
   measuring n-alkane of a number of different carbon numbers simultaneously;
   storing the mass number corresponding to the molecular weight of each n-alkane in a memory;
   preparing a mass chromatogram for each mass number that has been stored by a processor; and
   determining that the peak, where the ion intensity becomes a maximum in the mass chromatogram prepared focusing on each mass number, is the peak of the n-alkane having the molecular weight corresponding to this mass number by the processor.

2. The method according to claim 1, further comprising:
   displaying the retention time and the retention index of each n-alkane on a display.

* * * * *